(12) United States Patent
Gaskill-Fox et al.

(10) Patent No.: US 9,162,229 B2
(45) Date of Patent: Oct. 20, 2015

(54) MULTI-DIRECTIONAL SORTING WITH REDUCED CONTAMINATION IN A FLOW CYTOMETER

(71) Applicant: Bio-Rad Laboratories, Inc., Hercules, CA (US)

(72) Inventors: Nathan Michael Gaskill-Fox, Fort Collins, CO (US); Daniel N. Fox, Bellvue, CO (US); Rodney C. Harris, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 354 days.

(21) Appl. No.: 13/923,480

(22) Filed: Jun. 21, 2013

(65) Prior Publication Data

US 2013/0340539 A1     Dec. 26, 2013

Related U.S. Application Data

(60) Provisional application No. 61/663,030, filed on Jun. 22, 2012.

(51) Int. Cl.
*G01N 15/14* (2006.01)
*B01L 9/00* (2006.01)
*B01L 9/06* (2006.01)
*G01N 35/10* (2006.01)

(52) U.S. Cl.
CPC . *B01L 9/52* (2013.01); *G01N 15/14* (2013.01); *B01L 9/06* (2013.01); *G01N 35/1011* (2013.01); *G01N 2015/149* (2013.01)

(58) Field of Classification Search
CPC ............ B01L 9/06; B01L 9/52; G01N 15/14; G01N 2015/149
See application file for complete search history.

(56) References Cited

U.S. PATENT DOCUMENTS

| 4,009,435 | A | 2/1977 | Hogg |
| 4,667,830 | A | 5/1987 | Nozaki, Jr. et al. |
| 6,281,018 | B1 * | 8/2001 | Kirouac et al. ........ 436/63 |
| 7,282,707 | B1 | 10/2007 | Zanon |
| 2009/0107893 | A1 | 4/2009 | Schembri et al. |
| 2011/0033339 | A1 | 2/2011 | Muraki |

FOREIGN PATENT DOCUMENTS

JP          62167478          7/1987

OTHER PUBLICATIONS

Translation of JP 62167478.*

* cited by examiner

*Primary Examiner* — Peter Macchiarolo
*Assistant Examiner* — Nathaniel Kolb
(74) *Attorney, Agent, or Firm* — William W. Cochran; Cochran Freund & Young LLC

(57) ABSTRACT

Disclosed is a collection sled for collecting a waste droplet stream 122 in a waste stream catcher that is located below sample collectors. Contamination of collected samples is reduced by collecting the waste droplet stream at a position that is below the sample collectors. A waste trough is provided that gets progressively larger in a downward direction, which prevents backsplash of waste fluid from the collection cavity. Standard sample collector tubes, as well as 8-well strips and microscope slides can be used with the collection sled to collect sample particles.

11 Claims, 6 Drawing Sheets

MULTI-DIRECTIONAL SORTING WITH REDUCED CONTAMINATION IN A FLOW CYTOMETER

CROSS-REFERENCE TO RELATED APPLICATIONS

This application is based upon and claims priority to U.S. provisional application Ser. No. 61/663,030, filed Jun. 22, 2012, entitled "Multi-Directional Sorting with Reduced Contamination in a Flow Cytometer," which application is specifically incorporated herein by reference for all that it discloses and teaches.

This application is related to U.S. Provisional Patent Application Ser. No. 61/656,934, filed Jun. 7, 2012, by Daniel N. Fox, Susan Hunter, Nathan Michael Gaskill-Fox, Kevin P. Raley and Richard A. Miles, entitled "Automated and Accurate Drop Delay for Flow Cytometry," U.S. Provisional Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," U.S. Provisional Patent Application Ser. No. 61/663,026, filed Jun. 22, 2012, by Nathan M. Gaskill-Fox, Daniel. N. Fox and Rodney C. Harris, entitled "Two Station Sample and Washing System," U.S. Provisional Patent Application Ser. No. 61/663,033, filed Jun. 22, 2012, by Daniel N. Fox, Matthias J. G. Ottenberg and Kevin P. Raley, entitled "Condensed Geometry Nozzle for Flow Cytometry," and U.S. Provisional Patent Application Ser. No. 61/663,021, filed Jun. 22, 2012, by Daniel N. Fox and Nathan M. Gaskill-Fox, entitled "Fluid Mixing and Rinsing System for a Flow Cytometer." All of these applications are hereby specifically incorporated herein by reference, for all that they disclose and teach.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest. Sorting and analysis of these particles can provide valuable information to both researchers and clinicians. In addition, sorted particles can be used for various purposes to achieve a wide variety of desired results.

SUMMARY

An embodiment of the present invention may therefore comprise a collection sled for a flow cytometer comprising: a first sample collector located in a first position to collect samples from a first deflected droplet stream in the flow cytometer, the first sample collector having apertures that accept standard size sample collection tubes; a second sample collector located in a second position to collect samples from a second deflected droplet stream in the flow cytometer, the second sample collector having apertures that accept standard size sample collection tubes, the second sample collector spaced apart from the first sample collector to form a trough between the first sample collector and the second sample collector along a side portion of the first sample collector and a side portion of the second sample collector, the trough being aligned with the waste droplet stream so that the waste droplet stream passes through the trough into a cavity formed by the first sample collector and the second sample collector; a waste stream collector formed from the cavity between the first sample collector and the second sample collector that expands in a downward direction from the trough to prevent backsplash of waste fluid from waste droplets in the waste droplet stream and has a waste disposal port for disposing of waste fluid from the waste droplet stream.

An embodiment of the present invention may further comprise a method of collecting a waste droplet stream in a flow cytometer comprising: placing a first sample collector in a first position on a collection sled to collect sample particles from a first deflected droplet stream at a first collection location; placing a second sample collector adjacent to the first sample collector in a second position on the collection sled to collect samples from a second deflected droplet stream at a second collection location, the first sample collector and the second sample collector forming a trough and a cavity for collecting waste fluids from a waste droplet stream; aligning the trough with the waste droplet stream so that the waste droplet stream is collected below the first collection location of the first droplet stream and the second collection location of the second droplet stream; guiding the collection sled in a direction along a single axis so that sample particles from the first deflected droplet stream are collected in a plurality of first collection containers at the first collection location as the collection sled is moved in the direction along the single axis, and so that particles from the second deflected droplet stream are collected in a plurality of second collection containers at the second collection location, as the collection sled is moved in the direction along the single axis.

DETAILED DESCRIPTION OF THE EMBODIMENTS

Figure 1:
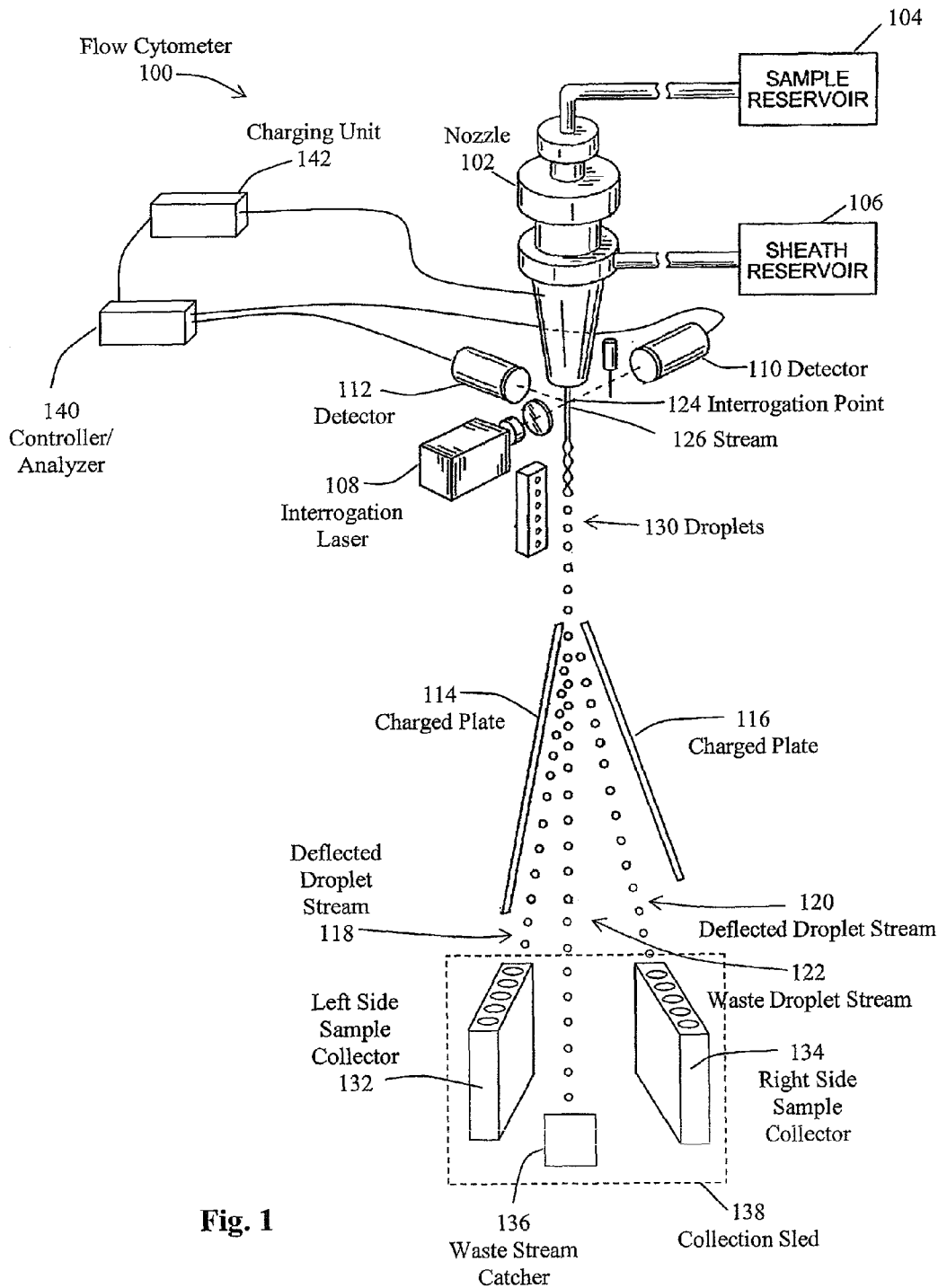
FIG. 1 is a schematic illustration of an embodiment of the present invention.

FIG. 1 is schematic illustration of an embodiment of a flow cytometer utilizing a collection sled 138 in accordance with one embodiment of the present invention. As illustrated in FIG. 1, the nozzle 102 generates a stream 126 that comprises sheath fluid from sheath reservoir 106 and sample fluid from sample reservoir 104. The stream 126 is interrogated by interrogation laser 108. Scattered light emitted by sample particles at integration point 124 may be detected by detector 110. Fluorescent emissions from sample particles at interrogation point 124 may be detected by detector 112. The stream 126 breaks off into droplets 130 that form a droplet stream. The droplets 130 are charged just prior to breaking off from the stream 126. Only the droplets that include particles to be sorted are charged. Controller/analyzer 140 is connected to the detectors 110, 112 and determines which droplets include particles of interest. The controller/analyzer 140 then provides a signal to the charging unit 142 to generate a charge on the stream 126 just prior to the droplet 130 breaking off from the stream 126. The remaining droplets are not charged and have a neutral polarity. The droplets containing particles of interest can receive either a negative or positive charge. Charged plates 114, 116 generate an electric field, which causes charged droplets to deflect into deflected droplet stream 118 and deflected droplet stream 120. The uncharged droplets are not deflected by the charged plates 114, 116 and form a waste droplet stream 122 that is collected in the waste stream catcher in the collection sled 138. The deflected droplet stream 118 is collected in the left side collector 132, while deflected droplet stream 120 is collected in right side sample collector 134.

Existing collectors have typically used a waste stream catcher that is located above the sample collectors, which allows the tray on which the sample collectors are located to move in two dimensions on x,y coordinates under the streams. In that manner, the sample collectors can be accurately positioned to effectively collect the sample. Existing systems have also provided movement of the sample collectors in an x,y plane to allow various types of collection containers to be used in the system. For example, it is desirable to use 5 mL test tubes, 8-well strips that can be formed into 96-well plates, and microscope slides. Existing systems have allowed movement of the collectors in an x,y plane to accommodate these three different types of collection container formats. If the waste stream catcher is located below the sample collectors, unrestricted movement in an x,y plane is not possible, since such movement would block the waste droplet stream. The problem that has been encountered with collecting the waste stream above the sample collectors is that, on occasion, the waste droplet stream 122 may become deflected for some reason, such as an obstruction in the opening in nozzle 102, incorrect nozzle alignment and other similar issues. When this occurs, the waste droplet stream may impact the edge of the waste stream catcher and cause splashing of waste particles that may land in the sample collectors. The sample is then contaminated, which produces an undesirable result. Increasing the size of the opening in the waste stream collector, and consequently the size of the waste stream collector, is not a practical solution, since the collection of the waste stream and the collection of the deflected streams must occur at a lower position, since the deflection angle is small. By lowering the collection points, less accuracy in the collection process is achieved. Also, collecting above the location of the sample collectors can result in other potential contamination issues, such as the waste stream collector being accidently mislocated while the waste droplet stream is running. Accordingly, the embodiment illustrated in FIG. 1 has a waste stream catcher 136 that is located below the left side sample collector 132 and right side sample collector 134. As explained below, the collection sled 138 moves in a single direction inwardly and outwardly from the flow cytometer 100 illustrated in FIG. 1.

Figure 2:
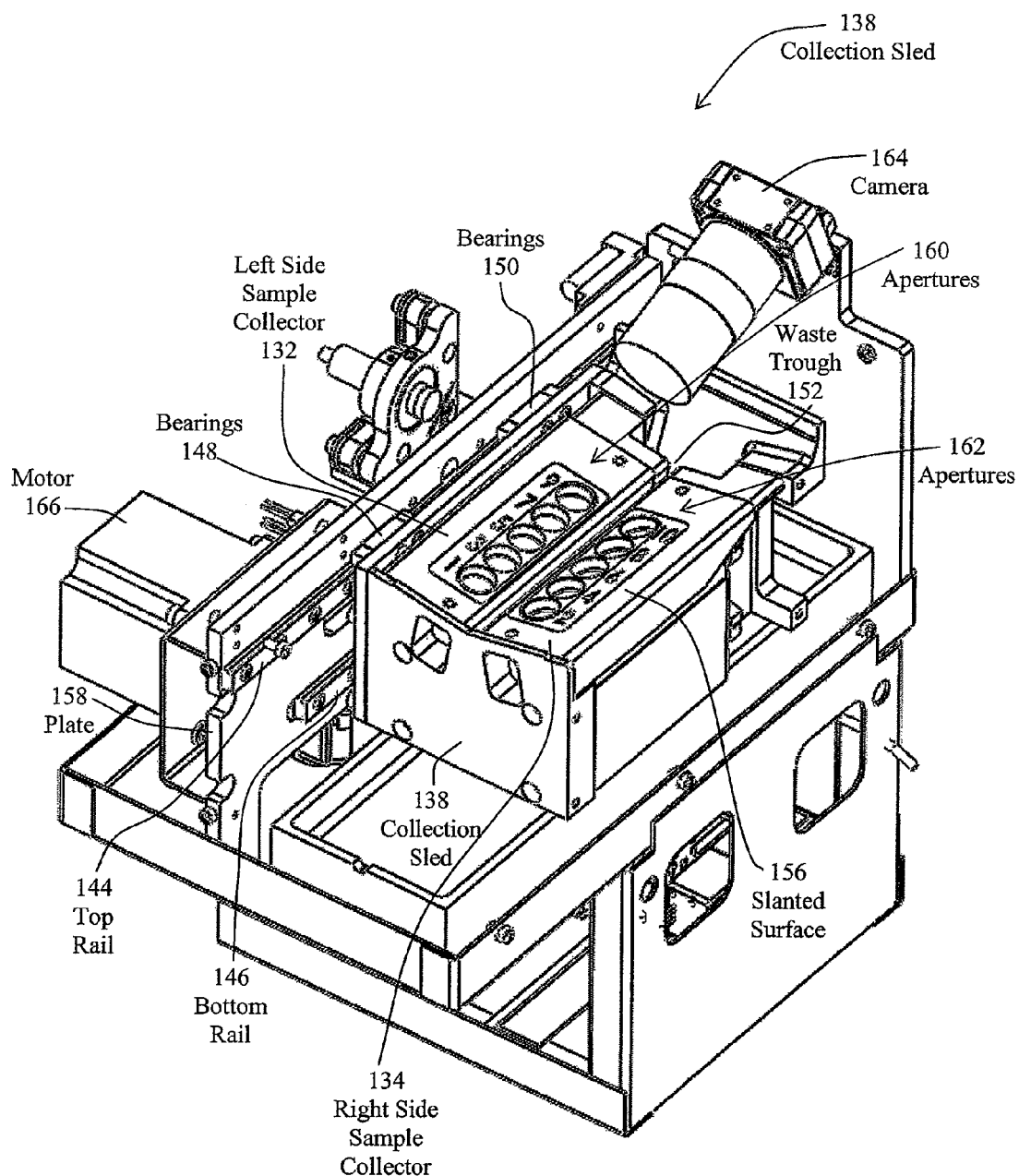
FIG. 2 is an isometric view of an embodiment of a collection sled and associated devices.

FIG. 2 is an isometric view of one embodiment of a waste stream catcher 136. As illustrated in FIG. 2, the waste stream catcher includes a collection sled 138 that is mounted on top rail 144 and bottom rail 146. Top rail 144 and bottom rail 146 are secured to plate 158. Bearings 148, 150 are mounted on top rail 144. Similar bearing 172 (FIG. 4) are mounted on the bottom rail 146. Bearings 148, 150, as well as bearing 172, are mounted to the side of the collection sled 138. The top rail 144 and bottom rail 146, as well as the bearings 148, 150, 172 allow the collection sled to move inwardly and outwardly in a single direction or axis in the flow cytometer. Apertures 160 are formed in the left side sample collector 132. Apertures 162 are formed in the right side sample collector 134. A waste trough 152 is located below apertures 160, 162. Apertures 160, 162 have a size and shape to accept a standard 5 mL sample collector, which is the most common form of sample collector. The surface of the collection sled 138 is a slanted surface 156, so that any fluids that are not properly collected flow into the waste trough 152. Camera 164 is a high resolution camera that records the location of the waste droplet stream 122 and the deflected droplet streams 118, 120. The apertures 160, 162 are sequentially aligned with the deflected droplet streams 118, 120 by motor 166. Motor 166 may comprise a stepper motor that is programmed to accurately align the apertures 160, 162 at the appropriate collection location for collecting the deflected droplet streams 118, 120. This process is done automatically using control signals generated by a processor that drives the motor 166.

Figure 3:
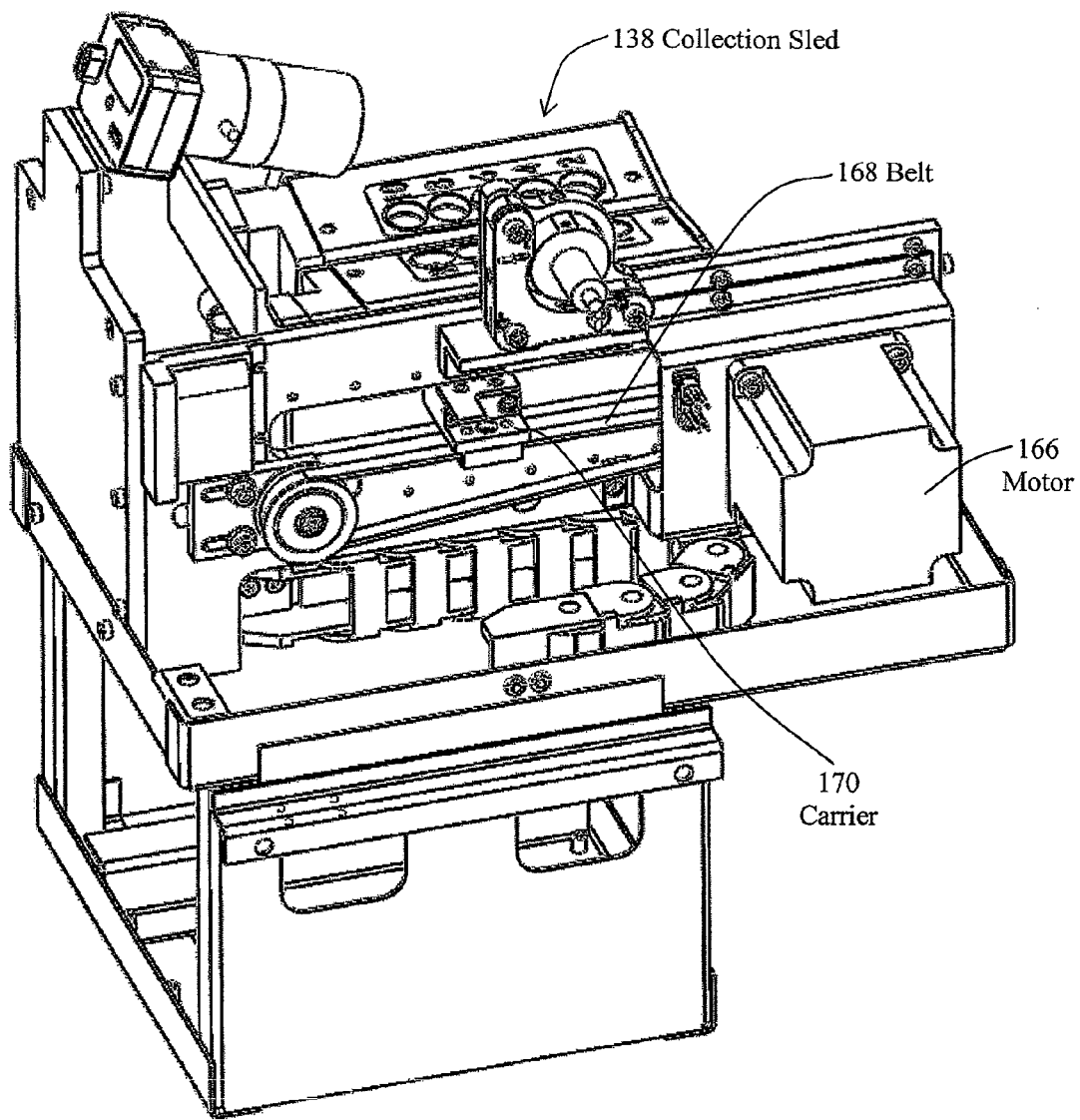
FIG. 3 is an isometric view of the embodiment of FIG. 2 viewed from a rear location.

FIG. 3 is an isometric view of the embodiment of FIG. 2, showing an alternate point of view. As shown in FIG. 3, motor 166 drives a belt 168. A carrier 170 is connected to the belt 168 and to the collection sled 138. Again, motor 166 may comprise a stepper motor that very accurately positions the collection sled 138 with regard to the deflected droplet streams 118, 120.

Figure 4:
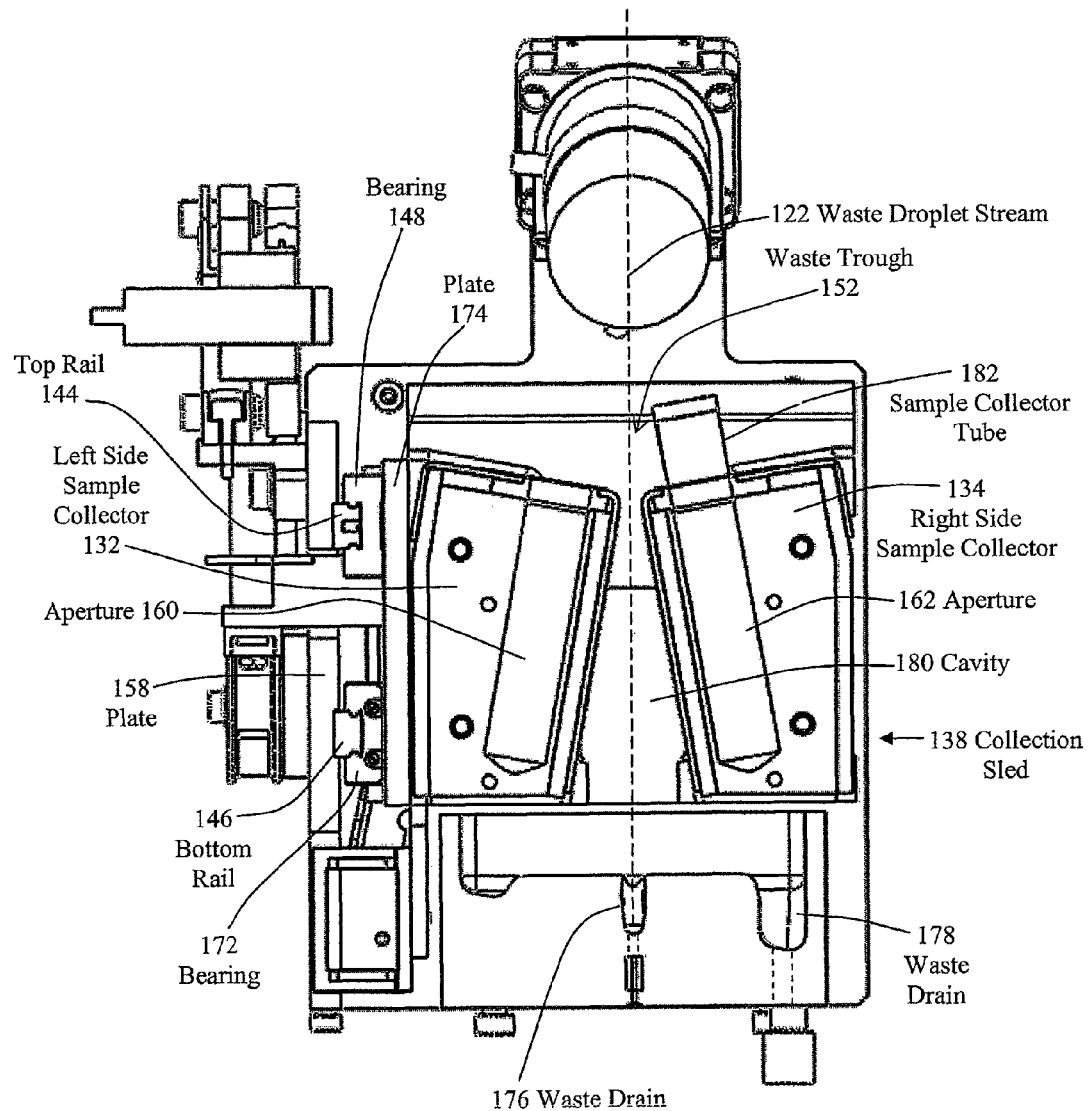
FIG. 4 is an end view of the embodiment of FIGS. 2 and 3.

FIG. 4 is an end view of the embodiment of FIGS. 2 and 3. As illustrated in FIG. 4, top rail 144 is engaged by bearing 148. Similarly, bottom rail 146 is engaged by bearing 172. Bearings 148, 172 are attached to the plate 174 that forms a portion of the collection sled 138. As illustrated in FIG. 4, the left side sample collector 132 is disposed in the collection sled 138 at a first angle. Similarly, right side sample collector 134 is disposed in the collection sled 138 at a similar opposite angle. The left side sample collector 132 and the right side sample collector 134 are spaced apart to form a waste trough 152. The opening of the waste trough 152 is narrowest at the top portion and expands to form a larger cavity 180. Waste drain 176 is aligned with the opening in the waste trough 152 to collect the waste droplet stream 122 that falls directly through the waste trough 152. Waste drain 176 is used in one example to collect calibration beads for calibrating the droplet separation location, as disclosed more fully in U.S. Provisional Application Ser. No. 61/656,934, filed Jun. 7, 2012, by Daniel N. Fox, Susan Hunter, Nathan Michael Gaskill-Fox, Kevin P. Raley, and Richard A. Miles, entitled "Automated and Accurate Drop Delay for Flow Cytometry," which is specifically incorporated herein by reference for all that it discloses and teaches. Waste drain 178 collects any other waste that collects in the cavity 180. Because the opening of the waste trough 152 is the smallest portion of the cavity 180, the waste droplet stream 122 does not splash upwardly and accidentally contaminate samples that are being collected on the left side sample collector 134. Further, sample collector tube 182 sits well above the opening of the waste trough 152 to prevent splashes from entering the opening of the sample collector tube 182. Apertures 160, 162 are specifically sized to accept standard 5 mL sample collector tubes, such as sample collector tube 182.

Figure 5:
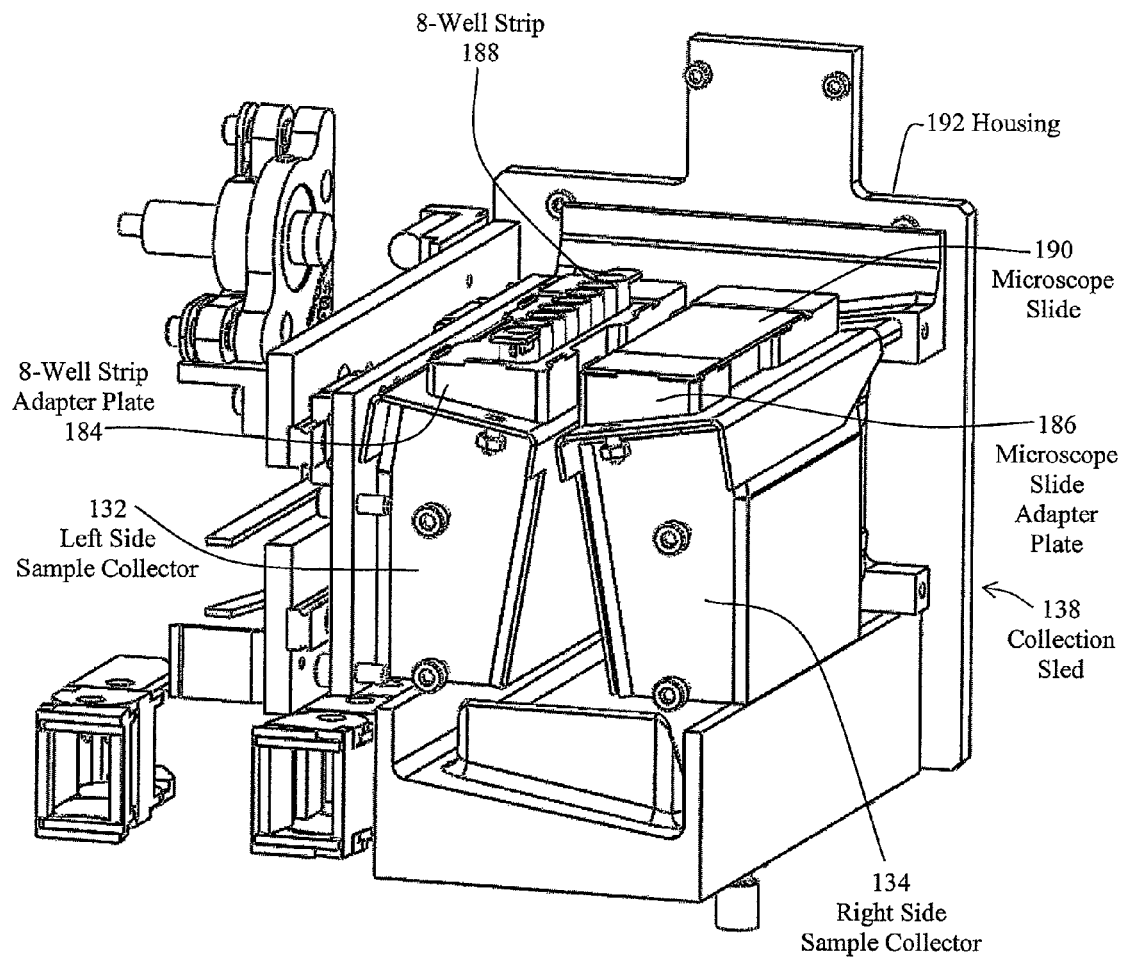
FIG. 5 is another isometric view of portions of the embodiment of FIGS. 2, 3 and 4.

FIG. 5 is another isometric view of the embodiment of FIGS. 2, 3 and 4, illustrating adapter plates 184, 186 that sit on the top portion of left side sample collector 132 and right side sample collector 134, respectively. As illustrated in FIG. 5, an 8-well strip is disposed in adapter plate 184 that is designed to mount an 8-well strip 188 in a collection location for collecting samples in the 8-well strip 188. Sample particles are deposited directly into compartments of the 8-well strip 188, as the collection sled 138 is moved inwardly and outwardly in housing 192. The 8-well strip 188 can be joined with other 8-well strips to form a 96-well plate that is commonly used in laboratories. The adapter plate 186 is illustrated with a microscope slide 190. In many instances, sorted cells may preferably be deposited on a microscope slide, such as microscope side 190. Different deposits can be made on the microscope slide 190, as the collection sled 138 is moved inwardly and outwardly on housing 192. The adapter plates 184, 186 are adapted to receive either the 8-well strip 188 or the microscope slide 190. The adapter plates 184, 186 are slanted to provide a flat, horizontal surface for mounting of the 8-well strip 188 and the microscope slide 190.

Figure 6:
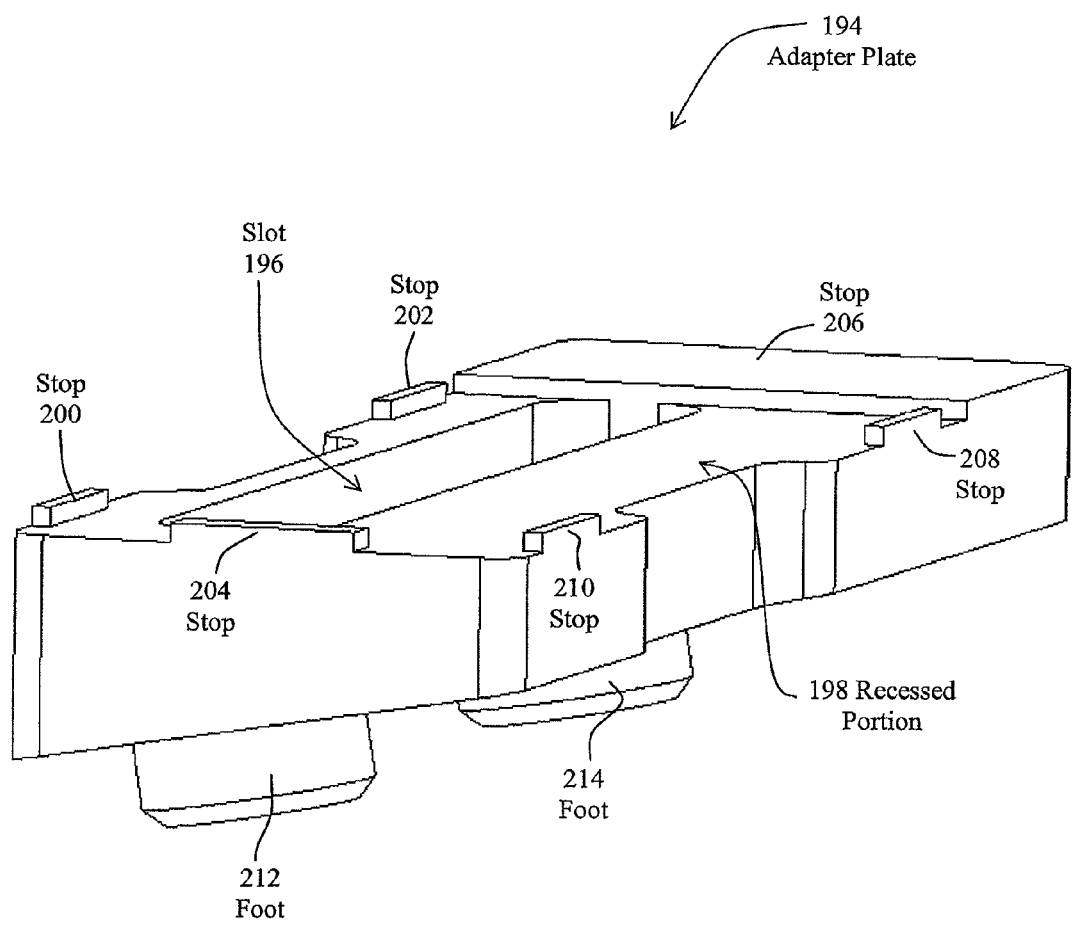
FIG. 6 is an isometric view of an embodiment of an adapter plate.

FIG. 6 is an isometric view of an embodiment of an adapter plate 194. As shown in FIG. 6, the adapter plate 194 includes a slot 196. The slot 196 is dimensioned to receive an 8-well strip, such as 8-well strip 188. The 8-well strip fits snuggly within the slot 916 and can be easily inserted and removed. The location of the 8-well strip in the slot 196 is referenced to the body of the adapter plate 194, so that the collection sled 138 can be accurately positioned, for sorting and depositing sample cells in the 8-well strip that is inserted in the slot 196. In addition, the adapter plate 194 includes a recessed portion 198. The recessed portion 198 is surrounded by stops 200, 202, 204, 206, 208, 210. The recessed portion 198 is sized so that a standard size microscope plate can be inserted in, and easily removed from, the recessed portion 198. Stops 200-210 hold the microscope slide 190 in a predetermined position so that sorted particles can be accurately located on positions of the microscope slide 190. Foot 212, as well as foot 214, accurately locate the adapter plate 194 on the left side sample collector 132 and right side sample collector 134, since the feet are adapted to be inserted in the apertures 160, 162 that are illustrated in FIG. 2. The adapter plate 194 is held in place on the surface of the sample collectors, as a result of foot 212 and foot 214 fitting precisely in the apertures 160, 162.

Hence, the embodiments disclosed herein provide a collection sled 138 that has a waste stream catcher 136 that is located below the sample collectors, such as left side sample collector 132 and right side sample collector 134. By locating the waste stream catcher 136 below the sample collectors, splashing and contamination of the waste droplet stream 122 is eliminated. Further, the sample collectors are positioned to form a waste trough 152 that extends along the length of the sample collectors and a waste cavity, since the waste trough extends along the length of the sample collectors 132, 134, at all locations on the collection sled 138, as the collection sled 138 is moved in a single direction in and out of the flow cytometer. The waste droplet stream 122 is collected in a cavity 180. The sample collector tube 182 is positioned above the waste trough, so that splashing of waste fluid into the sample collector tube does not occur. Additionally, the cavity 180 expands and gets progressively larger after the waste droplet stream 122 enters the waste trough 152, so that back splash of waste fluid does not occur. Further, an adapter plate is provided, which allows for collection of sample particles in an 8-well strip or a microscope slide. Accurate placement of the collection sled 138 is controlled by a stepper motor that is programmed to locate the sample collector tube 182, the 8-well strip 188, or the microscope slide 190 in the proper location for collection of sample particles. In this manner, the embodiments disclosed herein allow for collection of fluid using three different formats with the use of a single adapter. Further, contamination of collected samples is reduced because the waste stream catcher 136 is located below the sample collectors.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A collection sled for a flow cytometer comprising:
a first sample collector located in a first position to collect samples from a first deflected droplet stream in said flow cytometer, said first sample collector having apertures that accept standard size sample collection tubes;
a second sample collector located in a second position to collect samples from a second deflected droplet stream in said flow cytometer, said second sample collector having apertures that accept standard size sample collection tubes, said second sample collector spaced apart from said first sample collector to form a trough between said first sample collector and said second sample collector along a side portion of said first sample collector and a side portion of said second sample collector, said trough being aligned with said waste droplet stream so that said waste droplet stream passes through said trough into a cavity formed by said first sample collector and said second sample collector;
a waste stream collector formed from said cavity between said first sample collector and said second sample collector that expands in a downward direction from said trough to prevent backsplash of waste fluid from waste droplets in said waste droplet stream and has a waste disposal port for disposing of waste fluid from said waste droplet stream.

2. The collection sled of claim 1 further comprising:
a support structure that secures said first sample collector and said second sample collector;
a guide that is connected to said support structure that guides said support structure along a single axis so that said collection sled moves horizontally, inwardly and outwardly, in said flow cytometer at an angle that is substantially normal to said waste droplet stream.

3. The collection sled of claim 2 further comprising:
a motor that operates under a programmable control to move said collection sled so that said collection tubes are aligned with said first deflected droplet stream and said second deflected droplet stream.

4. The collection sled of claim 3 further comprising:
an adapter that has feet that fit in said apertures in said first sample collector and said second sample collector that is formed to provide a slot that accepts well strips and formed to have a recessed portion that accepts microscope plates.

5. A method of collecting a waste droplet stream in a flow cytometer comprising:
placing a first sample collector in a first position on a collection sled to collect sample particles from a first deflected droplet stream at a first collection location;
placing a second sample collector adjacent to said first sample collector in a second position on said collection sled to collect samples from a second deflected droplet stream at a second collection location, said first sample collector and said second sample collector forming a trough and a cavity for collecting waste fluids from a waste droplet stream, wherein said cavity expands in a downward direction from said trough to prevent backsplash of waste fluid from waste droplets in said waste droplet stream;

aligning said trough with said waste droplet stream so that said waste droplet stream is collected below said first collection location of said first droplet stream and said second collection location of said second droplet stream;

guiding said collection sled in a direction along a single axis so that sample particles from said first deflected droplet stream are collected in a plurality of first collection containers at said first collection location as said collection sled is moved in said direction along said single axis, and so that particles from said second deflected droplet stream are collected in a plurality of second collection containers at said second collection location, as said collection sled is moved in said direction along said single axis.

6. The method of claim 5 wherein said process of guiding said collection sled comprises:

coupling said collection sled to a guide that limits movement of said sled to said single axis so that said collection sled moves in a direction that is substantially normal to a direction of flow of said waste droplet stream.

7. The method of claim 6 further comprising:

using a motor to move said collection sled in said direction that is parallel to said single axis.

8. The method of claim 7 further comprising:

using an adapter that couples to said first sample collector and said second sample collector to collect said samples in a plurality of different types of collection containers.

9. The method of claim 8 wherein said process of using an adapter to collect samples in a plurality of different types of collection containers comprises:

using an adapter to collect samples in a sample collector tube.

10. The method of claim 8 wherein said process of using an adapter to collect samples in a plurality of different types of collection containers comprises:

using an adapter to collect samples in a well strip.

11. The method of claim 8 wherein said process of using an adapter to collect samples in a plurality of different types of collection containers comprises:

using an adapter to collect samples on a microscope slide.

\* \* \* \* \*